United States Patent [19]

Mao et al.

[11] Patent Number: 5,962,435

[45] Date of Patent: Oct. 5, 1999

[54] METHOD OF LOWERING SERUM CHOLESTEROL LEVELS WITH 2,6-DI-ALKYL-4-SILYL-PHENOLS

[75] Inventors: Simon J. T. Mao, Miaoli, Taiwan; Mark T. Yates; Roger A. Parker, both of Cincinnati, Ohio

[73] Assignee: Hoechst Marion Roussel, Inc., Bridgewater, N.J.

[21] Appl. No.: 08/854,647

[22] Filed: May 12, 1997

Related U.S. Application Data

[60] Division of application No. 08/582,835, Jan. 2, 1996, Pat. No. 5,677,291, which is a continuation-in-part of application No. 08/409,104, Mar. 27, 1995, abandoned, which is a continuation of application No. 08/165,281, Dec. 10, 1993, abandoned.

[51] Int. Cl.$^6$ ................................................. A61K 31/695
[52] U.S. Cl. .............................. 514/63; 556/447; 556/449
[58] Field of Search ............................... 514/63; 556/506, 556/447, 449

[56] References Cited

U.S. PATENT DOCUMENTS

| | | |
|---|---|---|
| 3,129,262 | 4/1964 | Laufer . |
| 3,328,450 | 6/1967 | Plueddemann . |
| 3,576,883 | 4/1971 | Neuworth . |
| 3,586,705 | 6/1971 | Owen et al. . |
| 3,786,100 | 1/1974 | Neuworth . |
| 3,862,332 | 1/1975 | Barnhart et al. . |
| 3,897,500 | 7/1975 | Neuworth . |
| 4,374,742 | 2/1983 | Evans et al. . |
| 4,663,314 | 5/1987 | Hayase et al. . |
| 4,670,421 | 6/1987 | DeVries et al. . |
| 4,719,237 | 1/1988 | McCaughan . |
| 4,734,527 | 3/1988 | Krauss . |
| 4,772,363 | 9/1988 | Van Effen . |
| 4,861,443 | 8/1989 | Van Effen . |
| 4,870,101 | 9/1989 | Ku et al. . |
| 4,900,757 | 2/1990 | Mao et al. . |
| 4,975,467 | 12/1990 | Ku et al. . |
| 5,008,421 | 4/1991 | Brownell et al. . |
| 5,061,734 | 10/1991 | Mao et al. . |
| 5,112,870 | 5/1992 | Mao et al. . |
| 5,117,028 | 5/1992 | Knorr . |
| 5,155,250 | 10/1992 | Parker et al. . |
| 5,217,870 | 6/1993 | Hession et al. . |
| 5,272,263 | 12/1993 | Hession et al. . |
| 5,281,738 | 1/1994 | Parker et al. . |
| 5,292,850 | 3/1994 | Pallini et al. . |
| 5,304,668 | 4/1994 | Parker et al. . |
| 5,356,917 | 10/1994 | Panetta . |
| 5,367,056 | 11/1994 | Hession et al. . |
| 5,380,747 | 1/1995 | Medford et al. . |
| 5,401,883 | 3/1995 | Laskovics et al. . |
| 5,532,400 | 7/1996 | Mao et al. . |

FOREIGN PATENT DOCUMENTS

| | | |
|---|---|---|
| 9460533 | 4/1993 | Australia . |
| 0374048 | 12/1989 | European Pat. Off. . |
| 0372542 | 6/1990 | European Pat. Off. . |
| 0464844 | 1/1992 | European Pat. Off. . |
| 0464852 | 1/1992 | European Pat. Off. . |
| 2308372 | 11/1976 | France . |
| 3604781 | 2/1986 | Germany . |
| 7330595 | 12/1995 | Japan . |
| 1199871 | 5/1978 | United Kingdom . |
| 2158450 | 4/1985 | United Kingdom . |
| 9312089 | 6/1993 | WIPO . |
| 9321914 | 11/1993 | WIPO . |
| 9405333 | 3/1994 | WIPO . |
| 9409772 | 5/1994 | WIPO . |
| 9411027 | 5/1994 | WIPO . |
| 9414786 | 7/1994 | WIPO . |
| 9416094 | 7/1994 | WIPO . |
| 9417828 | 8/1994 | WIPO . |
| 9504749 | 2/1995 | WIPO . |

*Primary Examiner*—Keith D. MacMillan
*Attorney, Agent, or Firm*—T. Helen Payne

[57] ABSTRACT

A method of lowering plasma cholesterol level in a patient with hypercholesterolemia, by administration of a compound of formula (1)

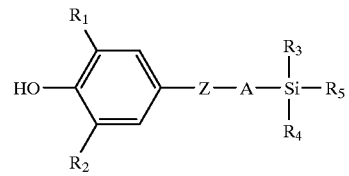

wherein:

$R_1$, $R_2$, $R_3$ and $R_4$ are each independently a $C_1$–$C_6$ alkyl group;

Z is a thio, oxy or methylene group;

A is a $C_1$–$C_4$ alkylene group; and $R_5$ is a $C_1$–$C_6$ alkyl or —$(CH_2)_n$—(Ar)

wherein n is an integer 0, 1, 2 or 3; and Ar is phenyl or napthyl unsubstituted or substituted with one to three substituents selected from the group consisting of hydroxy, methoxy, ethoxy, chloro, fluoro or $C_1$–$C_6$ alkyl.

10 Claims, No Drawings

METHOD OF LOWERING SERUM CHOLESTEROL LEVELS WITH 2,6-DI-ALKYL-4-SILYL-PHENOLS

This is a division, of application Ser. No. 08/582,835, filed Jan. 2, 1996, now U.S. Pat. No. 5,677,291 which is a continuation-in-part of application Ser. No. 08/409,104 filed Mar. 27, 1995, now abandoned; which is a continuation of application Ser. No. 08/165,281 filed Dec. 10, 1993, now abandoned; which is herein incorporated by reference.

Coronary heart disease (CHD) remains the leading cause of death in the industrialized countries. Despite recent declines in CHD mortality, CHD is still responsible for more than 500,000 deaths in the U.S. annually. It is estimated that CHD, directly and indirectly, costs the U.S. more than $100 billion a year. The primary cause of CHD is atherosclerosis, a disease characterized by the deposition of lipids in the arterial vessel wall, resulting in a narrowing of the vessel passages and ultimately hardening the vascular system.

Atherosclerosis as manifested in its major clinical complication, ischaemic heart disease, is thought to begin with local injury to the arterial endothelium followed by proliferation of arterial smooth muscle cells from the medial layer to the intimal layer along with deposition of lipid and accumulation of foam cells in the lesion. As the atherosclerotic plaque develops, it progressively occludes more and more blood vessel and can eventually lead to ischaemia or infarction. Therefore, it is desirable to provide a method of inhibiting the progression of atherosclerosis in patients in need thereof.

Hypercholesterolemia is an important risk factor associated with CHD. For example, in December 1984, a National Institute of Health Consensus Development Conference Panel concluded that lowering plasma cholesterol levels (specifically blood levels of low-density lipoprotein cholesterol) will definitely reduce the risk of heart attacks due to CHD. Serum lipoproteins are the carriers for lipids in the circulation. They are classified according to their density: chylomicrons, very low-density lipoproteins (VLDL), low density lipoproteins (LDL) and high-density lipoproteins (HDL). Chylomicrons mainly participate in transporting dietary triglycerides and cholesterol from the intestine to adipose tissue and liver. VLDL deliver endogenously synthesized triglycerides from liver to adipose and other tissues. LDL transports cholesterol to peripheral tissues and regulate endogenous cholesterol levels in those tissues. HDL transports cholesterol from peripheral tissues to the liver. Arterial wall cholesterol is derived almost exclusively from LDL (Brown and Goldstein, *Ann. Rev. Biochem.* 52, 223 (1983); Miller, *Ann. Rev. Med.* 31, 97 (1980)). In patients with low levels of LDL, the development of atheroscherosis is rare. Accordingly, it is desirable to provide a method for reducing plasma cholesterol in patients with hypercholesterolemia or at risk of developing hypercholesterolemia.

Elevated cholesterol levels are also associated with a number of disease states, including restenosis, angina, cerebral arteriosclerosis, and xanthoma. It is desirable to provide a method for reducing plasma cholesterol in patients with, or at risk of developing, restenosis, angina, cerebral arteriosclerosis, xanthoma, and other disease states associated with elevated cholesterol levels.

SUMMARY OF THE INVENTION

The present invention relates to the use of certain 2,6-di-alkyl-4-silyl-phenols to lower cholesterol levels in patients with hypercholesterolemia. The present invention also relates to the use of certain 2,6-di-alkyl-4-silyl-phenols to lower cholesterol levels in patients with restenosis, angina, cerebral artheriosclerosis, xanthoma and other disease states associated with elevated cholesterol levels.

The present invention relates to a method for lowering plasma cholesterol in a patient by administration of a compound of the formula of (1)

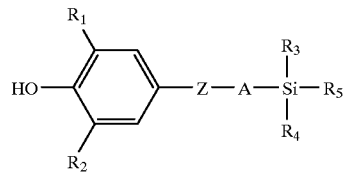

wherein:
$R_1$, $R_2$, $R_3$ and $R_4$ are each independently a $C_1$–$C_6$ alkyl group;
Z is a thio, oxy or methylene group;
A is a $C_1$–$C_4$ alkylene group; and
$R_5$ is a $C_1$–$C_6$ alkyl or —$(CH_2)_n$—(Ar)
wherein n is an integer 0, 1, 2 or 3; and Ar is phenyl or napthyl unsubstituted or substituted with one to three substituents selected from the group consisting of hydroxy, methoxy, ethoxy, chloro, fluoro or $C_1$–$C_6$ alkyl.

DETAILED DESCRIPTION OF THE INVENTION

As used herein, the term "$C_1$–$C_6$ alkyl" refers to a saturated hydrocarbyl radical of straight, branched or cyclic configuration made up of from one to six carbon atoms. Included within the scope of this term are methyl, ethyl, n-propyl, isopropyl, n-butyl, isobutyl, sec-butyl, tertiarybutyl, n-pentyl, n-hexyl, cyclohexyl and the like.

Likewise, the term "$C_1$–$C_4$ alkylene" refers to a saturated hydrocarbyldiyl radical of straight or branched configuration made up of from one to four carbon atoms. Included within the scope of this term are methylene, 1,2-ethane-diyl, 1,1-ethane-diyl, 1,3-propane-diyl, 1,2-propane-diyl, 1,3-butane-diyl, 1,4-butane-diyl and the like.

In those instances wherein $R_5$ is a —$(CH_2)n$—(Ar) radical, the "—$(CH_2)n$—" moiety represents a saturated hydrocarbyldiyl radical of straight chain configuration. The term "n" is defined as an integer 0, 1, 2 or 3. The moiety "—$(CH_2)_n$—" thus represents a bond, methylene, 1,2-ethanediyl or 1,3-propanediyl. The "—(Ar)" moiety represents an aryl radical defined as a substituted or unsubstituted phenyl or napthyl group. In those instances wherein the —(Ar) moiety is a substituted aryl, the phenyl or napthyl can bear from 1 to 3 substituents in any position otherwise occupied by a hydrogen atom. Substituents are selected from the group consisting of hydroxy, methoxy, ethoxy, chloro, fluoro and $C_1$–$C_6$ alkyl group. Specifically included within the scope of the term "—$(CH_2)_n$—(Ar)" are phenyl; napthyl; phenylmethyl; phenylethyl; 3,4,5-trihydroxyphenyl; 3,4,5-trimethoxyphenyl; 3,4,5-triethoxyphenyl; 4-chlorophenyl; 4-methylphenyl; 3,5-di-tertiarybutyl-4-hydroxyphenyl;4-fluorophenyl; 4-chloro-1-naphthyl; 2-methyl-1-naphthylmethyl; 2-naphthylmethyl; 4-chlorophenylmethyl; 4-tertiarybutylphenyl; 4-tertiarybutylphenylmethyl and the like.

The compounds of formula (1) can be prepared by utilizing procedures and techniques well known and appreciated by one of ordinary skill in the art. A general synthetic scheme for preparing compounds of formula (1) wherein Z is sulfur or oxygen is set forth in Scheme A, wherein all substituents, unless otherwise indicated, are previously defined.

Scheme A

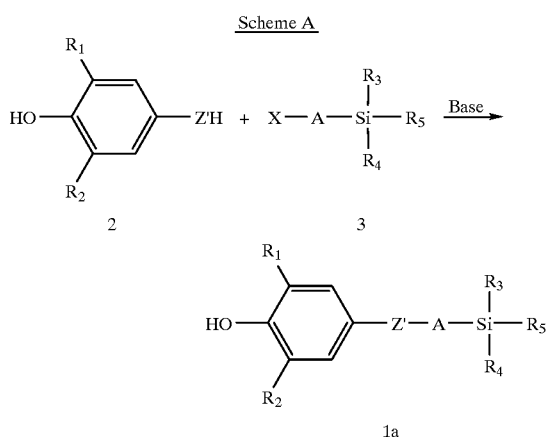

Z' = S or O
X = chlorine, bromine, or iodine

In general, a phenol of structure 1a can be prepared by reacting the appropriate 2,6-dialkyl-4-mercaptophenol or 2,6-dialkylhydroquinone of structure 2 (or suitably protected derivatives) with a non-nucleophilic base, such as sodium hydride, potassium carbonate or cesium carbonate, and the appropriate haloalkylenesilane of structure 3, such as the appropriate chloroalkylenesilane, in a suitable aprotic solvent, such as acetonitrile, dimethylformamide or dimethylacetamide, or in an aqueous solvent, such as water/2-butanone.

Starting materials for use in the general synthetic procedure outlined in Scheme A are readily available to one of ordinary skill in the art. For example, certain phenol starting materials for various compounds of formula (1) wherein Z is sulfur, such as 2,6-di-teriarybutyl-4-mercaptophenol, are described in U.S. Pat. No. 3,576,883, U.S. Pat. No. 3,952,064, U.S. Pat. No. 3,479,407 and in Japanese Patent Application 73-28425. Also, silyl starting materials for various compounds of formula (1), such as (trimethylsilyl)-methyl iodide, (trimethylsilyl)methyl bromide, (trimethyl-silyl) methyl chloride, (1-chloropropyl)trimethylsilane, are described in Synthesis 4, 318–19 (1988) and *J. Am. Chem. Soc.* 105, 5665–75 (1983). Additional methods for preparing suitable silanes include a Grignard reaction eg. 4-Bromoanisole is reacted with magnesium metat to form the Grignard reagent and the reagent is reacted with chlorodimethyl chloromethy (silane to give chloromethyldimethyl-4-methoxy phenyl silane.

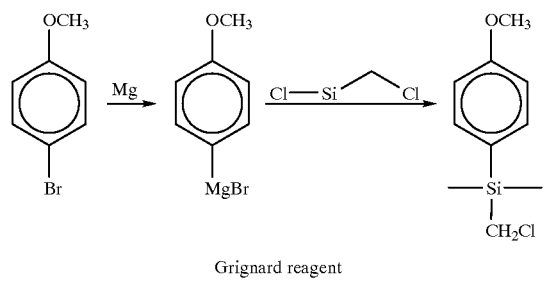

Grignard reagent

Alternatively, anisole may be lithiated by reacton with Δ-Butylithium and the lithio compound formed is reacted with chlorodimethyl chloromethyl silane to give chloromethyl dimethyl-2-methoxyphenyl silane.

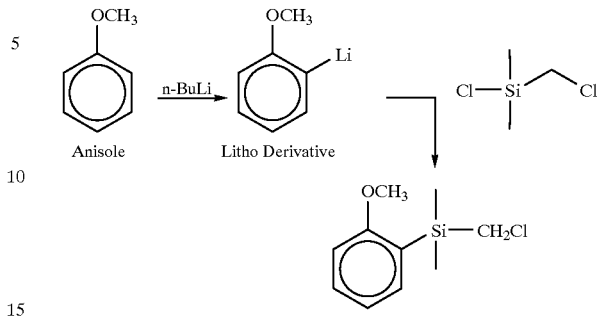

In those instances where the 1-phenol functionality of a compound of structure 2 may react with the compounds of structure 3 under the conditions of the reaction, the 1-phenol functionality of compound of structure 2 may be blocked with standard phenol blocking agents which are well known and appreciated in the art. The selection and utilization of particular blocking groups are well known to one of ordinary skill in the art. In general, blocking groups should be selected which adequately protect the phenol in question during subsequent synthetic steps and which are readily removable under conditions which will not cause degradation of the desired product.

Examples of suitable phenol protecting groups are ethers, such as methoxymethyl, 2-methoxyethoxymethyl, tetrahydro-pyranyl, t-butyl and benzyl; silyl ethers, such as trimethylsilyl and t-butyldimethylsilyl; esters, such as acetate and benzoate; carbonates, such as methylcarbonate and benzylcarbonate; as well as sulfonates, such as methanesulfonate and toluenesulfonate.

In those instances where $R_1$ and $R_2$ are each t-butyl, the reaction of Scheme A may be conveniently carried out without blocking of the 1-phenol functionality.

The following examples present typical syntheses as described in Scheme A. These examples are understood to be illustrative only and are not intended to limit the scope of the present invention in any way. As used herein, the following terms have the indicated meanings: "g" refers to grams; "mmol" refers to millimoles; "mL" refers to milliliters; "bp" refers to boiling point; "° C." refers to degrees Celsius; "mm Hg" refers to millimeters of mercury; "mp" refers to melting point; "mg" refers to milligrams; "μM" refers to micromolar; "μg" refers to micrograms.

EXAMPLE 1

2,6-Di-t-butyl-4[(dimethylphenylsilyl)methylthio] phenol (Compound A)

Mix 2,6-di-t-butyl-4-mercaptophenol (2.4 g, 10 mmol), potassium carbonate (1.4 g, 10 mmol), chloromethyldimethylphenylsilane (1.9 g, 10 mmol) and dimethylformamide (50 mL) and stir overnight at room temperature under argon atmosphere. Dilute the mixture with ice-water and extract with ethyl ether. Wash the ethereal layer with water, then brine, filter through flourosil-$Na_2SO_4$, and evaporate to an orange oil (3.5 g). Purify the product by first distilling (bp 160–170° C. @ 0.1 mm Hg), then subjecting to silica gel chromatography ($CCl_4$:$CHCl_3$/1:1) to obtain the title compound as a light yellow oil which slowly crystallizes to a white waxy solid (2.3 g, 59%). Anal. Calcd for $C_{23}H_{34}OSSi$: C, 71.44; H, 8.86; S, 8.29; Found: C, 71.14; H, 8.86; S, 7.98.

EXAMPLE 2

2,6-Di-t-butyl-4[(dimethyldodecylsilyl)methylthio] phenol (Compound B)

Mix 2,6-di-t-butyl-4-mercaptophenol (2.4 g, 10 mmol), potassium carbonate (1.7 g, 12.3 mmol), chloromethyldodecyldimethylsilane (2.8 g, 10 mmole) and dimethylformamide (50 mL) and stir overnight at room temperature under argon atmosphere. Dilute the mixture with ice-water, acidify with aqueous hydrochloric acid and extract with ethyl ether. Wash the ethereal layer with water, then brine, filter through fluorosil-$Na_2SO_4$ and evaporate to an orange semi-solid (4.0 g). Purify the product by first distilling (180–200° C. @ 0.1 mm Hg) then subjecting to silica gel chromatography ($CCl_4$) to obtain the title compound as a colorless oil which slowly crystallizes.

Anal. Calcd for $C_{29}H_{54}OSSi$: C, 72.73; H, 11.37; S, 6.70; Found: C, 71.26; H, 11.34; S, 6.93.

EXAMPLE 3

2,6-Di-t-butyl-4[(trimethylsilyl)methylthio]phenol (Compound C)

Mix 2,6-di-t-butyl-4-mercaptophenol (2.4 g, 10 mmol), potassium carbonate (1.4 g, 10 mmol), and dimethylacetamide (50 mL) and stir at room temperature under argon atmosphere. Add chloromethyltrimethylsilane (1.3 g, 10 mmol) and stir overnight. Warm on a steam bath for 2 hours, cool, and dilute with water. Extract with ethyl ether, dry, evaporate to a light yellow solid (2.8 g) and recrystallize ($CH_3CN$) to give 1.1 g (34%) of the title compound; mp 100–101° C.

Anal. Calcd for $C_{18}H_{32}OSSi$: C, 66.60; H, 9.88; S, 9.88; Found: C, 66.83; H, 10.05; S. 9.91.

EXAMPLE 4

2,6-Dimethyl-4[(trimethylsilyl)methyloxy]phenol (Compound D)

Mix 2,6-dimethylhydroquinone (1.4 g, 10 mmol), potassium carbonate (1.4 g, 10 mmol), chloromethyltrimethylsilane (1.9 g, 10 mmol) and dimethylformamide (50 mL). Stir at room temperature under inert atmosphere until the reaction is complete. Dilute the mixture with ice-water and extract with ethyl ether. Wash the ethereal layer with water, then brine and filter through fluorosil-$Na_2SO_4$. Evaporate to give the title compound and purify by silica gel chromatography.

EXAMPLE 5

2,6 Di-t-butyl-4[(4-chlorophenyldimethylsilyl)methyloxy]phenol (Compond E)

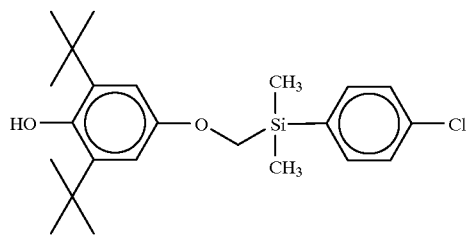

Reflux 2,6- di-t-butylbenzhydroquinone (13.7 g, 61.6 mM), potassium carbonate (9.4 g, 68 mM), chloromethyl (4-chlorophenyl) dimethyl silane ( 14.9 g, 68 mM) and a catalytic amount of potassium iodide in acetonitrile (200 ml) for three days under $N_2$. Filter off solids and evaporate. Redissolve in ethyl acetate and wash with water, then brine, dry with anhydrous magnesium sulfate, filter and evaporate. The resulting orange oil can be purified by distilling to 135° C. @ 0.1 mm Hg to remove lower boiling impurities followed by distillation of product (bp ° C. @ 0.1 mm Hg). The product which crystallizes on standing can be recrystallized from hexane to give fine white needles (7.4 g, 27% yield ) mp102–105° C.

Anal. Calcd. for $C_{23}H_{33}ClO_2Si$: C, 68.20; H, 8.21 Found: C, 68.39; H, 8.13 NMR (CDC13): 7.53 (d, 2H, J 8.3), 7.34 (d, 2H, J 8.3) 6.79 (s, 2H), 4.73 (s, 1H), 3.71 (s, 2H), 1.42 (s, 18H), 0.41 (s, 6H).

EXAMPLE 6

2,6 Di-t-butyl-4[dimethyl-4-fluorophenylsilyl)methyloxy]phenol (Compound F)

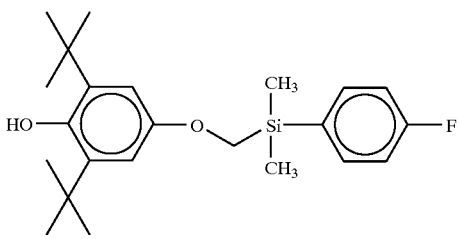

Reflux 2,6-di-t-butylbenzhydroquinone (10.0 g, 45 mM), potassium carbonate (6.2 g, 45 mM) and dimethyl (4-flurophenyl) iodomethylsilane (13.2 g, 45 mM) in acetonitrile (150 ml) for three days under nitrogen. Filter off solids and evaporate. Redissolve in ethyl acetate and wash with water, then brine, dry with anhydrous magnesium sulfate, filter and evaporate to a very pale yellow oil which crystallizes on standing. This material could be recrystallized from methanol to give a white crystalline solid (5.9 g, 34% yield) mp 90–93° C.

Anal. calcd. for $C_{23}H_{33}FO_2Si$: C, 71.09; H, 8.86 Found: C. 70.96; H, 8.58 NMR ($CDCl_3$): 7.58 (dd, 2H, J 8.5, 6.2), 7.10-7.04(m, 2H), 6.80(s, 2H), 4.73 (s, 1H), 3.71 (si, 2H), 1.43 (s, 18H), 0.41 (s, 6H).

EXAMPLE 7

2,6-Di-t-butyl-4[dimethylphenylsilyl)methyloxy] phenol (Compound G)

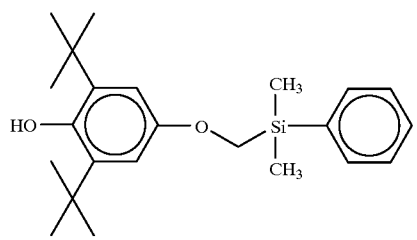

Reflux 2,6-di-t-butylbenzhydroquinone (5.43 g, 24.4 mM), potassium carbonate (3.7 g, 26.8 mM) and dimethyl (iodomethyl) phenylsilane (7.4 g, 26.8 mM) in acetonitrile (125 ml) overnight under $N_2$. Filter off solids and evaporate. Redissolve in ethyl acetate and wash with water, then brine, dry with anhydrous magnesium sulfate, filter and evaporate. The resulting orange oil can be purified by distilling to 135° C.@ 0.1 mm Hg. to remove lower boiling impurities followed by distillation of product (bp 155–165 C@ 0.1 mm Hg). The product which crystallizes on standing can be recrystallized from methanol to give a white solid (5.8g, 64% yield) mp 82–83° C.

Anal. Calcd. for $C_{23}H_{34}O_2Si$: C, 74.54; H, 9.25 Found: C, 74.51; H, 9.28 NMR ($CDCl_3$): 7.64–7.58 (m, 2H), 7.42–7.32 (m, 2H), 6.80 (s, 2H), 4.72 (s, 1H), 3.73 (s, 2H), 1.42 (s, 18H), 0.42 (s, 6H)

EXAMPLE 8

2,6-Di-t-butyl-4[(dimethyl-4-methoxy phenylsilyl) methyloxy]phenol (Compound H)

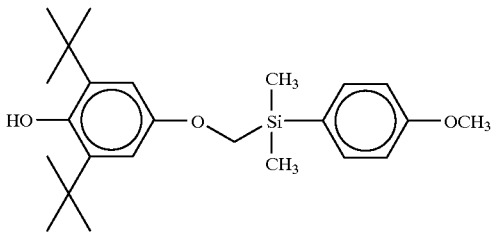

Reflux 2,6-di-t-butylbenzhydroquinone (13.7 g, 61.1 mM), potassium carbonate (9.4 g, 68 mM), chloromethyl (dimethyl)-4-methoxyphenylsilane (14.6 g, 68 mM) and a catalytic amount of potassium iodide in acetonitrile (200 ml) for three days under $N_2$. Filter off solids and evaporate. Redissolve in ethyl acetate and wash with water, then brine, dry with anhydrous magnesium sulfate, filter and evaporate. The resulting orange oil can be purified by distilling to 135° C. @ 0.1 mm Hg to remove lower boiling impurities followed by distillation of product (bp 155–165° C. @ 0.1 mm Hg). The product which crystallizes on standing can be recrystallized from hexane to give a white solid (4.9 g, 19% yield) mp 122–123° C.

Anal. Calcd. for $C_{24}H_{36}O_3Si$: C, 71.95; H, 9.06 Found: C, 71.80; H, 9.00 NMR (CDCl13): 7.53 (d, 2H, J 8.6), 6.93 (d, 2H, J8.6), 6.80 (s, 2H), 4.71 (s, 1H), 3.81 (s, 3H), 3.70 (s, 2H), 1.42 (s, 18H), 0.39 (s, 6H).

EXAMPLE 9

2,6-Dimethyl-4[(dimethylphenylsilyl)methyloxy] phenol (Compound I)

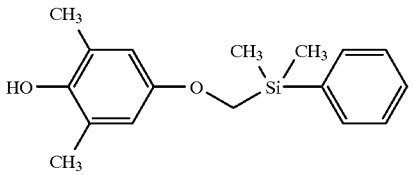

Reflux 2,6-dimethylhydroquinone (10.0 g, 72.4 mmol), potassium carbonate (10.0 g, 72.4 mmol), and dimethyl (chloromethyl)phenylsilane (13.4 g, 72.4 mmol in acetonitrile (150 ml) for 72 hours under argon. The mixture is allowed to cool and diluted with water and extracted into ether. The oil is distilled at 145° to 160° C. @ 0.1 mm Hg. to give 4.9 g. of a light yellow oil.

Anal. Calcd. for $C_{17}H_{22}O_2Si$: C, 71.28; H, 7.74 Found: C, 71.27; H, 7.74

EXAMPLE 10

2-t-butyl-6-methyl-4[(dimethylphenylsilyl) methylthio]phenol (Compond J)

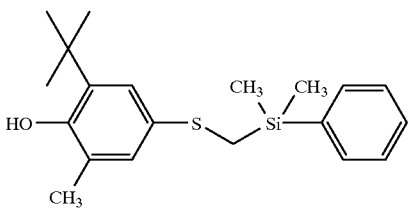

Reflux 2-t-butyl-6-methyl-4-mercaptophenol (11.8 g, 60.1 mmol), potassium bicarbonate (6.0 g, 11.8 mmol), and dimethyl(chloromethyl)phenylsilane (11.1 g 60.1 mmol) in isopropanol (150 ml) for 24 hours under argon. The mixture is allowed to cool and diluted with water and extracted into ether. The ether layer was evaporated to dryness to give 21.9 g of an oil. The oil is distilled at 145°–160° C. (0.1 mmHg) to give 5.5 g of a light yellow oil.

Anal. Calcd for $C_{20}H_{28}OSSi$: C, 69.71; H, 8.19 Found: C, 69.76, H, 8.20

EXAMPLE 11

2,6-Di-t-butyl-4-[(dimethy 1-2-methoxyphenylsilyl) methyloxy]phenol (Compound K)

A mixture of chloromethyldimethyl (2-methoxy) phenylsilane (27.2 g, 0.127 mole), sodium iodide (19 g, 0.127 mole) and acetonitrile (350 mL) was heated at reflux for 28 h. The mixture was cooled to ambient temperature and 2,6-di-t-butyl- 1, 4-hydroquinone (31.5 g, 0.14 mole) and potassium carbonate (20.8 g, 0.15) mole were added. The mixture was refluxed under a nitrogen atmosphere for 7 days. The mixture was cooled, poured into water (400 mL) and ethyl acetate (400 mL) and the organic layer was separated. The organic layer was evaporated and the residue was chromatographed on silica gel (hexane/ethyl acetate 9/1). The chromatographed product was recrystallized (methanol) to give the product (15.6 g, 31%) as a white solid, mp 89–90° C.

Anal. Calcd for $C_{24}H_{36}O_3Si$: C, 71.95; H, 9.06 Found: C, 71.84; H, 9.05.

EXAMPLE 12

2,6-Di-t-butyl-4-[(dimethyl-2, 5-dimethoxyphenylsilyl) methyloxy]phenol (Compound L)

Preparation as for previous compound using chloromethyl dimethyl-2, 5-dimethoxy-phenyl silane (14g, 57mmole) as the silane to give a white solid, mp 103°–04° C.

Anal. Calcd for $C_{25}H_{38}O_4Si$: C, 69.72; H, 8.89 Found: C, 69.71; H, 8.72.

EXAMPLE 13

2,6-Di-t-butyl-4-[(dimethyl-2, 3-dimethoxyphenylsilyl) methyloxy]phenol (Compund M)

Preparation as above using chloromethyl (dimethyl)-2,3-dimethoxy phenyl siland (11.3 g, 46 mmole) as the silane to give a white solid, mp 94.5–96°C.

Anal. Calcd for $C_{25}H_{38}O_4Si$: C, 69.72; H, 8.89 Found: C, 69.84; H, 8.91.

EXAMPLE 14

2,6-Di-t-butyl-4-[(dimethyl-4-t-butylphenylsilyl) methyloxy]phenol (Compound N)

Preparation as above using 4-t-Butylphenyl chloromethyl dimethyl silane (6.2 g, 25.7mmole) as the silane to give the product as a white solid, mp 114–115° C.

Anal. Calcd for $C_{27}H_{42}O_2Si$: C, 76.00; H, 9.92 Found: C, 75.94; H, 10.13.

EXAMPLE 15

2,6-Di-t-butyl-4-[(benzyldimethylsilyl) methyloxy] phenol (Compound O)

Preparation as above using benzyl chloromethyl dimethyl silane (7.13 g, 35.9 mmole) as the silane to give the product as a white solid, mp 76–77° C.

Anal. Calcd for $C_{24}H_{36}O_2Si$: C, 74.95; H, 9.43 Found: C, 74.94; H, 9.36.

The following compounds can be prepared by procedures analogous to those described above in Examples 1–15:

2,6-di-t-butyl-4[(triethylsilyl)methylthio]phenol
2,6-di-t-butyl-4[(diethylphenylsilyl)methylthio]phenol
2,6-di-t-butyl-4[(tripropylsilyl)methylthio]phenol
2,6-di-t-butyl-4[(dipropylphenylsilyl)methylthio]phenol
2,6-di-t-butyl-4[(triisopropylsilyl)methylthio]phenol
2,6-di-t-butyl-4[(diisopropylphenylsilyl)methylthio]phenol
2,6-di-t-butyl-4[(tributylsilyl)methylthio]phenol
2,6-di-t-butyl-4[(dibutylphenylsilyl)methylthio]phenol
2,6-di-t-butyl-4[(triisobutylsilyl)methylthio]phenol
2,6-di-t-butyl-4[(diisobutylphenylsilyl)methylthio]phenol
2,6-di-t-butyl-4[(tri-t-butylsilyl)methylthio]phenol
2,6-di-t-butyl-4[(di-t-butylphenylsilyl)methylthio]phenol
2,6-di-methyl-4[(trimethylsilyl)methylthio]phenol
2,6-di-methyl-4[(dimethylphenylsilyl)methylthio]phenol
2,6-di-methyl-4[(dibutylphenylsilyl)methylthio]phenol
2,6-di-methyl-4[(tri-t-butylsilyl)methylthio]phenol
2,6-di-methyl-4[(di-t-butylphenylsilyl)methylthio]phenol
2,6-di-ethyl-4[(trimethylsilyl)methylthio]phenol
2,6-di-ethyl-4[(dimethylphenylsilyl)methylthio]phenol
2,6-di-ethyl-4[(tri-t-butylsilyl)methylthio]phenol
2,6-di-ethyl-4[(di-t-butylphenylsilyl)methylthio]phenol
2,6-di-propyl-4[(trimethylsilyl)methylthio]phenol
2,6-di-propyl-4[(dimethylphenylsilyl)methylthio]phenol
2,6-di-isopropyl-4[(trimethylsilyl)methylthio]phenol
2,6-di-isopropyl-4[(dimethylphenylsilyl)methylthio]phenol
2,6-di-butyl-4[(trimethylsilyl)methylthio]phenol
2,6-di-butyl-4[(dimethylphenylsilyl)methylthio]phenol
2,6-dimethyl-4[(trimethylsilyl)methyloxy]phenol
2,6-dimethyl-4[(dimethylphenylsilyl)methyloxy]phenol
2,6-dibutyl-4[(triethylsilyl)methyloxy]phenol
2,6-dibutyl-4[(diethylphenylsilyl)methyloxy]phenol
2,6-di-t-butyl-4[(trimethylsilyl)methyloxy]phenol
2,6-di-t-butyl-4[(dimethylphenylsilyl)methyloxy]phenol.

A general synthetic scheme for preparing compounds of formula 1 wherein Z is methylene is set forth in Scheme B, wherein all substituents, unless otherwise indicated, are previously defined.

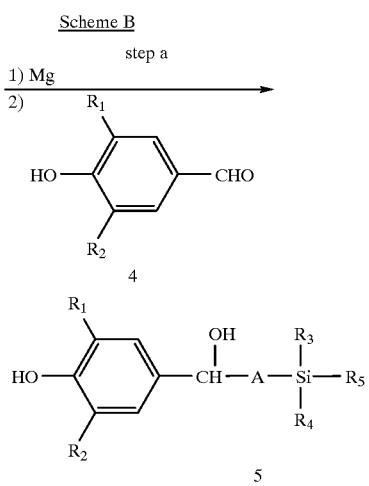

Scheme B

In general, a phenol of structure 1b can be prepared according to Scheme B in a two-step process. In step a, the appropriate haloalkylenesilane of structure 3 is reacted with magnesium metal in a suitable aprotic solvent, such as ethyl ether, in order to form the magnesium halide salt. The magnesium halide salt (Grignard reagent) is then reacted with the appropriate 3,5-dialkyl-4-hydroxy-benzaldehyde of structure 4 ( or a suitably protected derivative) to give the alcohol of structure 5. In step b, the alcohol of structure 5 can be reduced to the desired phenol of structure 1b by a variety of reduction techniques and procedures as are well known and appreciated in the art. For example, the alcohol of structure 5 can be reduced by means of a Birch reduction by reacting it with sodium in liquid ammonia.

Starting materials for use in the general synthetic procedures outlined in Scheme B are readily available or can readily be prepared according to standard techniques and procedures. Where necessary to prevent undesired side reactions, the 1-phenol functionality of the 3,5-dialkyl-4-hydroxy-benzaldehyde of structure 4 in Scheme B may be blocked prior to the Grignard reaction with a standard phenol blocking agent as described previously in Scheme A.

The following example presents a typical synthesis as described in Scheme B. This example is understood to be illustrative only and is not intended to limit the scope of the present invention in any way.

EXAMPLE 16

2,6-Dimethyl-4[2-(trimethylsilyl)ethyl]phenol (Compound P)

Step a: Mix magnesium turnings (240 mg, 10 mmol) and anhydrous ethyl ether under an inert atmosphere. Add a solution of chloromethyltrimethylsilane (1.9 g, 10 mmol) in anhydrous ethyl ether. Stir until the magnesium metal dissolves. Add a solution of 3,5-dimethyl-4-hydroxybenzaldehyde (1.5 g, 10 mmol) in anhydrous ethyl ether. Stir until reaction is complete. Cool the reaction mixture to 0° C. and add saturated ammonium chloride solution. Separate the ether layer, wash with water and dry ($MgSO_4$). Evaporate to give 4-hydroxy-3,5-dimethyl-α-[(trimethylsilyl)-methyl]benzenemethanol and purify by silica gel chromatography.

Step b: Mix sodium metal (520 mg, 22.6 mmol) and liquid ammonia (13 mL). To this solution add, by dropwise addition, a solution of 4-hydroxy-3,5-dimethyl-α-

[(trimethylsilyl)-methyl]benzenemethanol (2.22 g, 10 mmol) in ethyl alcohol (O.5 g) and ethyl ether (5 ml). After the blue color disappears, cautiously add water (13 mL), extract with ethyl ether, dry (MgSO$_4$), and evaporate the solvent. Purify the residue by silica gel chromatography to yield the title compound.

Alternatively, compounds of formula (1) wherein Z is methylene can be prepared according to the procedure set forth in Scheme C, wherein all substituents, unless otherwise indicated, are previously described.

Scheme C

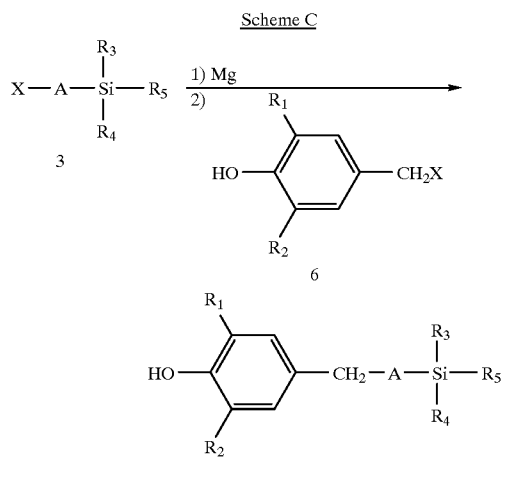

In general, a phenol of structure 1b can be prepared by first reacting the appropriate haloalkylenesilane of structure 3 with magnesium metal in an suitable aprotic solvent, such as ethyl ether, in order to form the magnesium halide salt. The magnesium halide salt (Grignard Reagent) is then reacted with the appropriate 3,5-dialkyl-4-hydroxy-benzylhalide of structure 6 (or a suitably protected derivative) to give the desired phenol of structure 1b.

Starting materials for use in the general synthetic procedures outlined in Scheme C are readily available or can readily be prepared according to standard techniques and procedures. For example, the preparation of 3,5-dimethyl-4-acetoxy-benzylbromide is described in *Tetrahedron* 33, 3097–103 (1977). 3,5-Dimethyl-4-acetoxy-benzylbromide can be converted to the corresponding phenolic starting material by standard hydrolytic procedures.

Where necessary to prevent undesired side reactions, the 1-phenol functionality of the 3,5-dialkyl-4-hydroxy-benzylhalide of structure 6 in Scheme C may be blocked prior to the Grignard reaction with a standard phenol blocking agent as described previously in Scheme A.

The following example presents a typical syntheses as described in Scheme C. his example is understood to be illustrative only and is not intended to limit the scope f the present invention in any way.

EXAMPLE 17

2,6-diethyl-4-[2-(trimethylsilyl)ethyl]-phenol (Compound Q)

Mix magnesium turnings (240 mg, 10 mmol) and anhydrous ethyl ether under an inert atmosphere. Add a solution of chloromethyltrimethylsilane (1.9 g, 10 mmol) in anhydrous ethyl ether. Stir until the magnesium metal dissolves. Add a solution of 4-bromomethyl-2,6-diethylphenol (2.43g, 10mmol) in anhydrous ethyl ether and reflux the mixture until the reaction is complete. Pour onto a mixture of ice/hydrochloric acid and separate the layers. Wash the ethereal layer with water, dry (MgSO$_4$) and evaporate to give the title compound which is purified by silica gel chromatography.

The following compounds can be prepared by procedures analogous to those described above in Example 17:
2,6-dipropyl-4-[2-(trimethylsilyl)ethyl]-phenol
2,6-dipropyl-4- [2-(dimethylphenylsilyl)ethyl]-phenol
2,6-diisopropyl-4-[2-(trimethylsilyl)ethyl]-phenol
2,6-diisopropyl-4-[2-(dimethylphenylsilyl)ethyl]-phenol
2,6-diisobutyl-4-[2-(trimethylsilyl)ethyl]-phenol
2,6-diisobutyl-4-[2-(dimethylphenylsilyl)ethyl]-phenol
2,6-dibutyl-4- [2-(trimethylsilyl)ethyl]-phenol
2,6-dibutyl-4- [2-(dimethylphenylsilyl)ethyl]-phenol
2,6-di-t-butyl-4-[2-(trimethylsilyl)ethyl]-phenol
2,6-di-t-butyl-4-[2-(dimethylphenylsilyl)ethyl]-phenol
2,6-di-t-butyl-4-[2-(tri-t-butylsilyl)ethyl]-phenol
2,6-di-t-butyl-4- [2-(di-t-butylphenylsilyl)ethyl]-phenol
5 2,6-dimethyl-4-[2-(trimethylsilyl)ethyl]-phenol
2,6-dimethyl-4-[2-(dimethylphenylsilyl)ethyl]-phenol.

It is understood that compounds of formula (1) may exist in various stereoisomeric forms. All stereoisomeric forms which are consistent with the above structural formulas, as interpreted according to standard conventions for expressing stereoisomeric structure, are intended to be included within the scope of the present invention.

Compounds of formula (1), e.g. 2,6-di-alkyl-4-silyl-phenols, are known in the art. Specifically, compounds of formula (1) are described in U.S. Pat. No. 5,155,250. Preferred compounds of formula (1) are those in which $R_1$ and $R_2$ are $C_4$ alkyl group, $R_3$ and R4 are a $C_1$ alkyl group, A is a $C_1$ alkylene group, and $R_5$ is —$(CH_2)_n$—(Ar) where n is 0 and Ar is phenyl unsubstituted or substituted with one to three substituents selected from the group consisting of hydroxy, methoxy, ethoxy, chloro, fluoro or $C_1$–$C_6$ alkyl. More preferred is the compound 2,6-di-t-butyl-4 [(dimethylphenyl-silyl)methyl]-thio-phenol.

As used herein, the term "patient" refers to warm-blooded animals or mammals, including rabbits and humans, who are in need of lowering plasma cholesterol levels or in need of lowering plasma LDL levels.

Hypercholesterolemia is a disease state characterized by the excessive cholesterol levels in the blood. The identification of patients with hypercholesterolemia and who are in need of treatment is well within the ability and knowledge of one skilled in the art. For example, individuals who are either suffering from clinically significant hypercholesterolemia or who are at risk of developing clinically significant hypercholesterolemia are patients in need of treatment. A clinician skilled in the art can readily determine, by the use of clinical tests, physical examination and medical/family history, if an individual is a patient in need of treatment for hypercholesterolemia.

An effective amount of a compound of formula (1) is an amount which is effective in inhibiting development or growth of hypercholesterolernia in a patient in need thereof. As such, successful treatment of a patient for hypercholesterolemia is understood to include effectively reducing or lowering serum cholesterol levels in a patient's blood and does not necessarily indicate a total elimination of the cholesterol. It is further understood and appreciated by those skilled in the art that successful treatment or hypercholesterolemia includes the use as a prophylactic to prevent clinically significant elevated levels of serum cholesterol.

An effective amount of a compound of formula (1) can be readily determined by the use of conventional techniques and by observing results obtained under analogous circumstances. In determining the effective dose, a number of factors are considered including, but not limited to: the species of patient; its size, age, and general health; the specific disease involved; the degree of or involvement or the severity of the disease; the response of the individual patient; the particular compound administered; the mode of administration; the bioavailability characteristics of the preparation administered; the dose regimen selected; and the use of concomitant medication.

An effective amount of a compound of formula (1) will generally vary from about 1 milligram per kilogram of body weight per day (mg/kg/day) to about 5 grams per kilogram of body weight per day (gm/kg/day). A daily dose of from about 1 mg/kg to about 500 mg/kg is preferred.

In effecting treatment of a patient, a compound of formula (1) can be administered in any form or mode which makes the compound bioavailable in effective amounts, including oral and parenteral routes. For example, the compound can be administered orally, subcutaneously, intramuscularly, intravenously, transdermally, intranasally, rectally, and the like. Oral administration is generally preferred. One skilled in the art of preparing formulations can readily select the proper form and mode of administration depending upon the disease state to be treated, the stage of the disease, and other relevant circumstances.

A compound of formula (1) can be administered in the form of pharmaceutical compositions or medicaments which are made by combining a compound of formula (1) with pharmaceutically acceptable carriers or excipients, the proportion and nature of which are determined by the chosen route of administration, and standard pharmaceutical practice.

The pharmaceutical compositions or medicaments are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The pharmaceutical compositions may be administered orally, for example, with an inert diluent or with an edible carrier. They may be enclosed in gelatin capsules or compressed into tablets. For the purpose of oral therapeutic administration, a compound of formula (1) may be incorporated with excipients and used in the form of tablets, troches, capsules, elixirs, suspensions, syrups, wafers, chewing gums and the like. These preparations should contain at least 4% of a compound of formula (1), the active ingredient, but may be varied depending upon the particular form and may conveniently be between 4% to about 70% of the weight of the unit. The amount of the active ingredient present in compositions is such that a unit dosage form suitable for administration will be obtained.

The tablets, pills, capsules, troches and the like may also contain one or more of the following adjuvants: binders, such as microcrystalline cellulose, gum tragacanth or gelatin; excipients, such as starch or lactose, disintegrating agents such as alginic acid, Primogel, corn starch and the like; lubricants, such as magnesium stearate or Sterotex; glidants, such as colloidal silicon dioxide; and sweetening agents, such as sucrose or saccharin may be added or flavoring agents, such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active ingredient, sucrose as a sweetening agent and certain preservatives, dyes and colorings and flavors. Materials used in preparing these various compositions should be pharmaceutically pure and non-toxic in the amounts used.

For the purpose of parenteral administration, a compound of formula (1) may be incorporated into a solution or suspension. These preparations should contain at least 0.1% of a compound of the invention, but may be varied to be between 0.1 and about 50% of the weight thereof. The amount of the active ingredient present in such compositions is such that a suitable dosage will be obtained.

The solutions or suspensions may also include one or more of the following adjuvants depending on the solubility and other properties of a compound of formula (1): sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diamlnetetraacetic acid; buffers such as acetates, citrates or phosphates and agents for the adjustment of toxicity such as sodium chloride or dextrose. The parenteral preparation can be enclosed in ampules, disposable syringes or multiple dose vials made of glass or plastic.

The following examples illustrate the use of compounds of formula (1) according to the present invention. These examples are illustrative only and are not intended to limit the scope of the invention in any way.

EXAMPLE 18

Reduction of Cholesterol Levels of 1% Cholesterol-Fed New Zealand White Rabbits by Concurrent Administration of 0.5% Compound A (2,6-Di-t-butyl-4[(dimethylphenylsilyl)methylthio]phenol)

New Zealand White (NZW) rabbits (female, aged 3–4 months, weighing less than 3 kg) six in each group, were fed a control diet of 1% cholesterol (100 g rabbit chow daily containing 1 g cholesterol) or a diet of 1% cholesterol/0.5% drug (100 g rabbit chow daily containing 1 g cholesterol and 0.5 g Compound A). After 56 days, the rabbits were sacrificed by intravenous injection of pentobarbital. Plasma or serum was collected and cholesterol levels were determined using the enzymatic method of Mao, et al., *Clin. Chem.* (1983) 29: 1890–1897. The results obtained are summarized in Table 1, below:

| DAY | Control (n = 6) Cholesterol (mg/dl) | Compound A (n = 6) Cholesterol (mg/dl) |
|---|---|---|
| 0  | 61 ± 9      | 59 ± 8     |
| 14 | 1138 ± 134  | 684 ± 99   |
| 28 | 1908 ± 256  | 954 ± 126  |
| 42 | 2175 ± 376  | 1118 ± 164 |
| 56 | 2432 ± 475  | 1035 ± 152 |

At day 56, the reduction of serum cholesterol was 57% by the administration of Compound A.

EXAMPLE 19

Reduction of Cholesterol levels of 0.2% Cholesterol-Fed New-Zealand White Rabbits by Concurrent Administration of 0.4% Compound A NZW rabbits (female, aged 3–4 months, weighing less than 3 Kg), six in each group, were fed a control diet of 0.2% cholesterol (100 g rabbit chow daily containing 0.2 g cholesterol) or a diet of 0.2% cholesterol/0.4% drug (100 g rabbit chow daily containing 0.2 g cholesterol and 0.4 g Compound A). After 56 days, the rabbits were sacrificed by intravenous injection of pentobarbital. Plasma or serum was collected and cholesterol levels were determined using the enzymatic method of Mao, et al., *Clin. Chem.* (1983) 29: 1890–1897. The results obtained are summarized in Table 2 below:

| DAY | Control (n = 6) Cholesterol (mg/dl) | Compound A (n = 6) Cholesterol (mg/dl) |
|---|---|---|
| 0 | 73 ± 10 | 66 ± 8 |
| 7 | 325 ± 43 | 154 ± 17 |
| 14 | 587 ± 71 | 223 ± 32 |
| 28 | 898 ± 126 | 291 ± 59 |
| 42 | 988 ± 147 | 357 ± 89 |
| 56 | 941 ± 163 | 337 ± 100 |

The results obtained demonstrate that administration of Compound A for 56 days produced significant cholesterol lowering in 0.2% cholesterol-fed rabbits. The reduction of cholesterol was 64%.

EXAMPLE 20

Reduction of Cholesterol levels of 0.2% Cholesterol-Fed New Zealand White Rabbits by Concurrent Administration of 0.4% Drug NZW rabbits (female, aged 3–4 months, weighing less than 3 Kg), six in each group, were fed a control diet of 0.2% cholesterol (100 g rabbit chow daily containing 0.2 g cholesterol) or a diet of 0.2% cholesterol/0.4% drug (100 g rabbit chow daily containing 0.2 g cholesterol and 0.4 g of drug). For Compound A, the rabbits were sacrificed by intravenous injection of pentobarbital after 56 days. For Compound G, K, E and H, the rabbits were sacrificed by intravenous injection of pentobarbital after 7 days. Plasma or serum was collected and cholesterol levels were determined using the enzymatic method of Mao, et al., *Clin. Chem.* (1983) 29: 1890–1897. Liver weight and body weights were determined. Serum HDL and LDL cholesterol levels were determined using gel filtration HPLC modified from Kieft, K. A., et al., *J. Lipid Res.,* 32: 859–861 (1991), using Roche enzymatic cholesterol reagents. Triglyceride levels were determined by Cobas Automated Analyzer using Roche enzymatic reagents.

The results obtained are summarized in Table 2 below:

| Compound | liver wt/ body wt ratio | cholesterol (total) % Control | LDL cholesterol % Control | HDL cholesterol % Control | triglycerides |
|---|---|---|---|---|---|
| A | 120% | 52% | 42% | 75% | 366% |
| G | 104% | 72% | 69% | 81% | 104% |
| K | 90% | 77% | 61% | 217% | 131% |
| E | 93% | 87% | 89% | 109% | 82% |
| H | 110% | 54% | 66% | 123% | 73% |

EXAMPLE 21

Reduction in Cholesterol Levels of Normolipidemic New Zealand Rabbits by Concurrent Administration of 0.5% Compound A New Zealand White rabbits (female, aged 3–4 months, weighing less than 3 kg), four in each group, were fed a normal diet (100 g rabbit chow daily) or a diet of 0.5% drug (100 g rabbit chow daily containing 0.5 g Compound A). Serum was collected and cholesterol levels were determined according to the method of Mao, et al., *Clin. Chem.* (1983) 29: 1890–1897. The results are summarized in Table 3 below:

| DAY | Control (n = 4) Cholesterol (mg/dl) | Compound A (n = 4) Cholesterol (mg/dl) |
|---|---|---|
| 0 | 47.0 ± 11 | 45.3 ± 4 |
| 8 | 90.0 ± 13 | 69.7 ± 6 |
| 14 | 87.3 ± 7 | 54.8 ± 8 |
| 23 | 81.5 ± 68 | 58.3 ± 6 |

As compared to control rabbits at day 23, the level of cholesterol was significantly reduced by about 29%.

What is claimed is:

1. A compound selected from the group consisting of
   2,6-Di-t-butyl-4[(4-chlorophenyldimethylsilyl)methyloxy]phenol;
   2,6-Di-t-butyl-4[dimethyl-4-fluorophenylsilyl)methyloxy]phenol;
   2,6-Di-t-butyl-4[dimethylphenylsilyl)methyloxy]phenol;
   2,6-Dimethyl-4[(dimethylphenylsilyl)methyloxy]phenol;
   2-t-butyl-6-methyl-4[(dimethylphenylsilyl)methylthio]phenol;
   2,6-Di-t-butyl-4-[(dimethyl-2,5-dimethoxyphenylsilyl)methyloxy]phenol;
   2,6-Di-t-butyl-4-[(dimethyl-2,3-dimethoxyphenylsilyl)methyloxy]phenol;
   2,6-Di-t-butyl-4-[(dimethyl-4-t-butylphenylsilyl)methyloxy]phenol; and
   2,6-Di-t-butyl-4-[(benzyldimethylsilyl)methyloxy]phenol.

2. A compound according to claim 1 wherein the compound is 2,6-Di-t-butyl-4[(4-chlorophenyldimethylsilyl)methyloxy]phenol.

3. A compound according to claim 1 wherein the compound is 2,6-Di-t-butyl-4[dimethyl-4-fluorophenylsilyl)methyloxy]phenol.

4. A compound according to claim 1 wherein the compound is 2,6-Di-t-butyl-4[dimethylphenylsilyl)methyloxy]phenol.

5. A compound according to claim 1 wherein the compound is 2,6-Dimethyl-4[(dimethylphenylsilyl)methyloxy]phenol.

6. A compound according to claim 1 wherein the compound is 2-t-butyl-6-methyl-4[(dimethylphenylsilyl)methylthio]phenol.

7. A compound according to claim 1 wherein the compound is 2,6-Di-t-butyl-4-[(dimethyl-2,5-dimethoxyphenylsilyl)methyloxy]phenol.

8. A compound according to claim 1 wherein the compound is 2,6-Di-t-butyl-4-[(dimethyl-2,3-dimethoxyphenylsilyl)methyloxy]phenol.

9. A compound according to claim 1 wherein the compound is 2,6-Di-t-butyl-4-[(dimethyl-4-t-butylphenylsilyl)methyloxy]phenol.

10. A compound according to claim 1 wherein the compound is 2,6-Di-t-butyl-4-[(benzyldimethylsilyl)methyloxy]phenol.

* * * * *